US006112110A

United States Patent [19]
Wilk

[11] Patent Number: 6,112,110
[45] Date of Patent: Aug. 29, 2000

[54] MEDICAL TREATMENT SYSTEM WITH SCANNER INPUT

[76] Inventor: Peter J. Wilk, 185 W. End Ave., New York, N.Y. 10023

[21] Appl. No.: 09/249,946

[22] Filed: Feb. 12, 1999

Related U.S. Application Data

[62] Division of application No. 08/779,406, Jan. 7, 1997, Pat. No. 5,899,857.

[51] Int. Cl.$^7$ ........................................................ A61B 5/00
[52] U.S. Cl. ........................... 600/407; 600/411; 600/427; 607/100; 607/101
[58] Field of Search ..................................... 600/407, 411, 600/425, 427, 439; 607/100, 101; 601/2.4

[56] References Cited

U.S. PATENT DOCUMENTS

| 4,315,514 | 2/1982 | Drewes et al. | 600/427 |
|---|---|---|---|
| 5,305,748 | 4/1994 | Wilk | 600/407 |
| 5,464,013 | 11/1995 | Lemelson | 600/427 |

*Primary Examiner*—Ruth S. Smith
*Attorney, Agent, or Firm*—R. Neil Sudol; Henry D. Coleman

[57] ABSTRACT

A noninvasive medical treatment system includes a support for supporting a patient in a predetermined position and a frequency generator for generating essentially monochromatic electromagnetic energy of a frequency selected from a plurality of different treatment frequencies predetermined to selectively destroy organic molecules of respective types specific to a plurality of different kinds of human tissue. A selector is operatively connected to the frequency generator for selecting the one frequency from among the different treatment frequencies produceable by the frequency generator. The system further comprises radiation transmission and guidance components disposed between the frequency generator and the support for directing the energy from the frequency generator to predetermined target tissues internal to the patient supported on the support and for concentrating the energy on the target tissues. A scanner is disposed proximate to the support for obtaining three-dimensional data as to an organic structure internal to the patient so as to enabling a positional tracking of the target region. The scanner including means for continually updating the three-dimensional data during a medical treatment procedure. A computer is operatively connected to the scanner for continually monitoring location and shape of the organic structure during the medical treatment procedure. The computer is operatively connected to at least one of the frequency generator, the transmission and guidance components, and the support for controlling that element in response to the three-dimensional data from the scanner during the medical treatment procedure so that the energy impinges on the target tissues for sufficient time to effectively eradicate the target tissues, whereby the medical treatment procedure is performed despite movement of the organic structure during the medical treatment procedure.

14 Claims, 4 Drawing Sheets

MEDICAL TREATMENT SYSTEM WITH SCANNER INPUT

This is a division of application Ser. No. 08/779,406 filed Jan. 7, 1997 now U.S. Pat. No. 5,899,857.

BACKGROUND OF THE INVENTION

This invention relates to a medical treatment system. More particularly, this invention relates to a medical treatment system with scanner input. Even more particularly, this invention relates to an automatic treatment system with control based upon scanner input. This invention also relates to an associated method.

Substantial advances have been made in the last twenty years in ascertaining internal organic structures without surgery. CAT scanners and nuclear magnetic resonance (NMR) imaging devices, as well as ultrasonography, have provided the physician with powerful tools for use in diagnosing patients. For the most part, these scanners have been used solely in medical examinations and diagnosis. However, radiological treatment of brain tumors has used imaging equipment to locate target tumors and to direct radiation to the target location. In addition, U.S. Pat. No. 5,207,223 discloses the directing of a necrosis-causing X-ray beam to cancerous target tissues upon the locating of the target tissues by the comparison, with reference data, of electronic images garnished by diagnostic beams.

Such radiation-utilizing noninvasive surgical procedures have been limited to the treatment of tumorous growths. It would be enormously beneficial to the medical industry and to many patients if such noninvasive surgical techniques were available to treat other kinds of other kinds of tissues (e.g., otherwise healthy tissues) in other kinds of surgical procedures.

OBJECTS OF THE INVENTION

An object of the present invention is to provide an improved technique and an associated system for the treatment of structures internal to a patient.

Another object of the present invention is to provide such a technique and/or such a system which utilizes data obtained with a three-dimensional scanning apparatus.

Another, more particular, object of the present invention is to provide such a technique and/or associated system wherein control of surgical operations is automatic.

Yet another particular object of the present invention is to provide such a technique and/or such a system for the treatment of abscesses and/or tumors.

Other objects of the present invention will be apparent from the detailed descriptions and drawings included herein.

SUMMARY OF THE INVENTION

A noninvasive medical treatment system comprises, in accordance with the present invention, a support for supporting a patient in a predetermined position and a frequency generator for generating essentially monochromatic electromagnetic energy of a frequency selected from a plurality of different treatment frequencies predetermined to selectively destroy organic molecules of respective types specific to a plurality of different kinds of human tissue. A selector is operatively connected to the frequency generator for selecting the one frequency from among the different treatment frequencies produceable by the frequency generator. The system further comprises radiation transmission and guidance components disposed between the frequency generator and the support for directing the energy from the frequency generator to predetermined target tissues internal to the patient supported on the support and for concentrating the energy on the target tissues. A scanner is disposed proximate to the support for obtaining three-dimensional data as to an organic structure internal to the patient so as to enabling a positional tracking of the target region. The scanner including means for continually updating the three-dimensional data during a medical treatment procedure. A computer is operatively connected to the scanner for continually monitoring location and shape of the organic structure during the medical treatment procedure. The computer is operatively connected to at least one of the frequency generator, the transmission and guidance components, and the support for controlling that element in response to the three-dimensional data from the scanner during the medical treatment procedure so that the energy impinges on the target tissues for sufficient time to effectively eradicate the target tissues, whereby the medical treatment procedure is performed despite movement of the organic structure during the medical treatment procedure.

In accordance with a feature of the present invention, the computer includes means for identifying a location and a shape of the organic structure after a shift of the organic structure, based upon the three-dimensional data from the scanner. The computer exemplarily contains an identification module formed by generic computer circuit as modified by programming. The computer further includes a coordinate determination module for determining a change in positional coordinates of the target tissues due to the shift of the organic structure and for determining an operational modification of the controlled element (one of the frequency generator, the transmission and guidance components, and the support) for delivering the energy to the target tissues after the shift of the organic structure.

Generally, the frequency generator can produce each of i he various treatment frequencies. Accordingly, the system additionally comprises an operator control operatively connected to the frequency generator for selecting from among the different treatment frequencies.

The transmission and guidance components generally include a focusing element. Of course, where different treatment frequencies are produced by the frequency generator, the focusing element is able to direct and focus each frequency. The computer may control the focusing element to redirect or refocus a selected treatment frequency after a shift of the organic structure and, concomitantly, the target region.

The transmission and guidance components generally include means for directing the selected frequency from different directions to the target tissues. To this end, there may be a plurality of frequency generating components generating respective beams of radiation. Alternatively, beam splitters and reflectors may be provided for directing the selected monochromatic radiation to the target region from different directions through the patient's body.

Depending on the particular tissue and organ being treated in a noninvasive surgical method according to the present invention, one or several different treatment frequencies may be selected to irradiate the surgical site during the treatment procedure. One or more target molecules extant in cells in the target tissues are selected for irradiation. The treatment frequencies selected are spectral frequencies of the target molecules. Accordingly, the molecules absorb the radiation at the respective treatment frequencies and undergo physical and chemical changes which result in cell disruption. With the disruption of sufficient target cells, a recess or void may be generated in internal tissues, without incisions being made in the patient.

In an exemplary type of operation pursuant to the present invention, channels are formed in the myocardium from the left ventricle. The channels terminate in the myocardium, i.e., do not traverse the myocardium, for purposes of artificially vascularizing the tissues of the heart, as disclosed in U.S. Pat. No. 5,429,144. In this operation, the computer monitors the beating heart and activates the frequency generator, or otherwise enables the transmission and focusing of treatment radiation on a predetermined target region in the myocardium, in coordination or synchronization with the cardiac contractions. Every time the heart pauses between successive contractions, the treatment frequency is focused on the target region. During cardiac contraction, the computer interrupts transmission of the selected frequency to the target region.

In other kinds of operations, involving a slow movement of an internal organ such as the colon, the computer can move the support to realign the target region with the focal point of the radiation transmission and guidance components. Alternatively, the focusing element(s) may be actuated to adjust the focal point of the radiation to coincide with the shifted target region.

In accordance with another feature of the present invention, one or more photodetectors are disposed proximately to the support for sensing electromagnetic radiation emitted from the target tissues in response to excitation thereof by the selected treatment frequency. The computer is operatively connected to the photodetector(s) for detecting a change in spectral output of the target tissues in response to the selected treatment frequency and for interrupting the directing of the selected treatment frequency to the target tissues upon detecting such a change.

In a more specific embodiment of the invention, the frequency generator is capable of generating essentially monochromatic electromagnetic energy of two frequencies simultaneously, the selector being operatively connected to the frequency generator for selecting the two frequencies from among the different treatment frequencies produceable by the frequency generator. The transmission and guidance components are disposed between the frequency generator and the support for directing the two frequencies from the frequency generator to the predetermined target tissues internal to the patient supported on the support and for concentrating the energy on the target tissues.

A medical treatment method comprises, in accordance with the present invention, the steps of (a) supporting a patient in a predetermined position, (b) automatically scanning the patient, (c) determining, in response to the step of scanning, positional coordinates of a three-dimensional target region which is internal to the patient, (d) operating a frequency generator to (I) select a predetermined frequency from among a plurality of different treatment frequencies produceable by the frequency generator and predetermined to be absorbable by organic molecules of respective types specific to a plurality of different kinds of human tissue and (ii) to generate essentially monochromatic electromagnetic energy of the selected treatment frequency, (e) directing the predetermined frequency to the target region, in accordance with the positional coordinates, (f) concentrating the predetermined frequency on the target region, (g) continuing to automatically scan the patient, and (h) automatically ceasing the directing of the predetermined frequency to the target region upon detecting a change in location of target region in response to the continued automatic scanning of the patient.

In one procedure pursuant to the invention, the method further comprises automatically determining new positional coordinates of the target region after the change in location thereof, automatically redirecting the predetermined frequency to the changed location of the target region in accordance with the new positional coordinates, and concentrating the predetermined frequency on the changed location of the target region.

In one procedure pursuant to the invention, the method further comprises automatically determining when the target region has again attained the positional coordinates after the change in location of the target region, automatically redirecting the predetermined frequency to the target region when the target region has again attained the positional coordinates, and again concentrating the predetermined frequency on the target region when the target region has again attained the positional coordinates.

A technique and an associated system in accordance with the present invention for the treatment of structures internal to a patient enables the treatment of abscesses and tumors and the formation of vascularizing channels in the myocardium without conventional surgery, i.e., without the formation of extensive incisions. Such a technique reduces the durations of hospitalization stays and decreases patient trauma and thus reduces the expenses of surgical treatment.

A system and method in accordance with the present invention utilizes data obtained with a continuous scanning apparatus. Thus, the gathering of information and the control of surgical operations may be at least partially automated.

DETAILED DESCRIPTION

Figure 1:
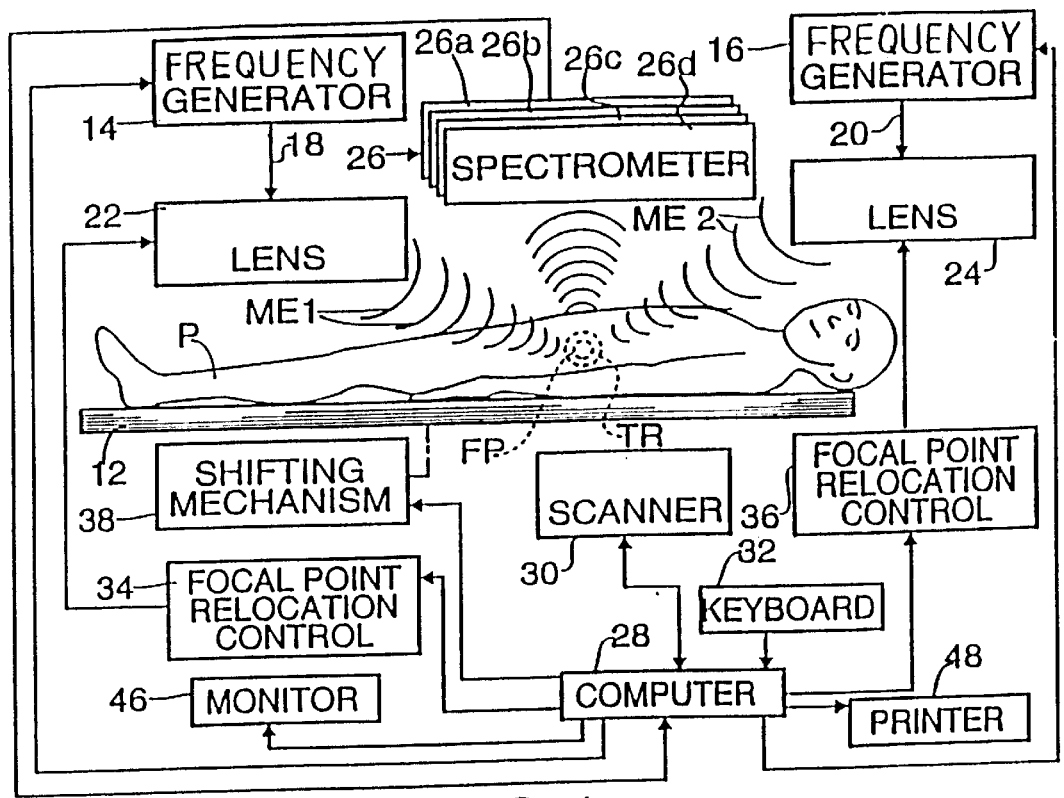
FIG. 1 is a block diagram of a medical treatment system in accordance with the present invention.

As illustrated in FIG. 1, a medical treatment system comprises a support 12 for supporting a patient P in a predetermined position and a plurality of radiation generators 14 and 16 for generating essentially monochromatic electromagnetic energy having one or more distinct frequencies in the microwave, near millimeter, infrared, optical, ultraviolet regions of the electromagnetic spectrum. Each radiation generator 14 and 16 is connected via a wave guide 18 or 20 to a respective focusing device or lens 22 or 24. Lenses 22 and 24 are disposed between the respective radiation generator 14 and 16 and patient support 12 for concentrating the electromagnetic treatment frequency or frequencies, e.g., microwaves ME1 and ME2, on a predetermined focal point FP internal to a target region TR inside patient P.

A computer 28 is operatively connected to a CAT scanner or NMR type imaging apparatus 30, possibly supplemented with ultrasonic imaging, juxtaposed to patient support 12. Scanner 30 provides computer 28 with continuously updated three-dimensional structural data as to the organs of patient P surrounding target region TR.

Computer 28 is also connected to peripheral output devices such as a monitor 46 and a printer 48 (FIG. 1) for communicating to an operator, e.g., a surgeon, the results of three-dimensional scans of patient P. Computer 28 receives additional input from a keyboard 32 and possible other devices such as a mouse (not illustrated). Viewing three-dimensional scanned organic structure of patient P on monitor 46 and/or on a print-out from printer 48, the surgeon or other operator selectively defines target region TR of patient P via keyboard 32 and the other instruction input devices (not shown) operatively linked to computer 28.

Keyboard 32 is also used to instruct computer 28 as to which frequency or frequencies are to be emitted from generators 14 and 16 for treating tissues in target region TR of patient P. The different treatment frequencies are selectively absorbable by organic molecules of respective types specific to a plurality of different kinds of human tissue. Generally, the treatment frequency or frequencies selected for tissues in target region TR are absorbed with the result of destroying the absorbing molecules and disrupting cell physiology and structure. Necrosis sets in and the target region is eventually cleared of the disrupted cells by natural physiological processes.

Target region TR may be additionally or alternatively defined by computer 28 in accordance with programming for the automatic identification of internal organic structures based on such previously defined parameters as shape, texture, density, and location relative to other organs. More specifically, computer 28 may automatically identify the location and general shape of a possible target region, the identification being implemented, for example, by a color coded outline on monitor 46. The surgeon then uses keyboard 32 and/or other input devices to more precisely define the boundaries of target region TR Computer 28 is connected to generators 14 and 16 for controlling such parameters as the rate of pulsing, the interpulse interval, the pulse duration and the intensity of the radiation. These radiation parameters may be preset by an operator via keyboard 32 and accord with the particular treatment procedure. Alternatively, the surgeon or operator may identify the type of procedure to computer 28 and the computer automatically selects the values of radiation parameters. For example, if target region TR is an abscess which is to be sterilized, computer 28 may automatically select the rate of pulsing, the interpulse interval, the pulse duration and the intensity of the radiation, as well as multiple radiation treatment points throughout target region TR. A different selection of such parameters is made by computer 28 in the event that the target region is a tumor to be removed via radiation treatment.

In addition, the spectral range of the energy produced by generators 14 and 16 may be adjusted in response to signals from computer 28. Furthermore, computer 28 may be instructed via keyboard 32 to automatically vary the output of generators 14 and 16 during a single treatment procedure on patient P.

It is to be noted that a plurality of generators 14 and 16, with their respective focusing lenses 22 and 24, are provided in part to minimize the amount of radiation absorbed by tissues outside of target region TR. It is only at focal point FP that the energy is sufficiently intense to cause destruction of biological cells, for example, in the case of a tumor, or a predetermined rise in temperature, for example, for the sterilization of fluid in an abscess.

As further illustrated in FIG. 1, computer 28 is connected to a pair of focal point relocation control units 34 and 36 in turn connected to respective lenses 22 and 24. In response to signals from computer 28, control units 34 and 36 can change the location of focal point FP in accordance with a sequence determined by the surgeon or by computer 28 pursuant to instructions from the surgeon, thereby enabling an automatic destruction or heating of cellular or organic material within target region TR. The excitation process can be continued until the tissues or fluids of target region TR are destroyed or sterilized.

As an alternative or supplement to relocation control units 34 and 36, a shifting mechanism 38 is connected to patient support 12 and computer 28 for shifting the position of the patient P under the control of computer 28, thereby changing the location of the focal point FP relative to patient P.

Figure 2:
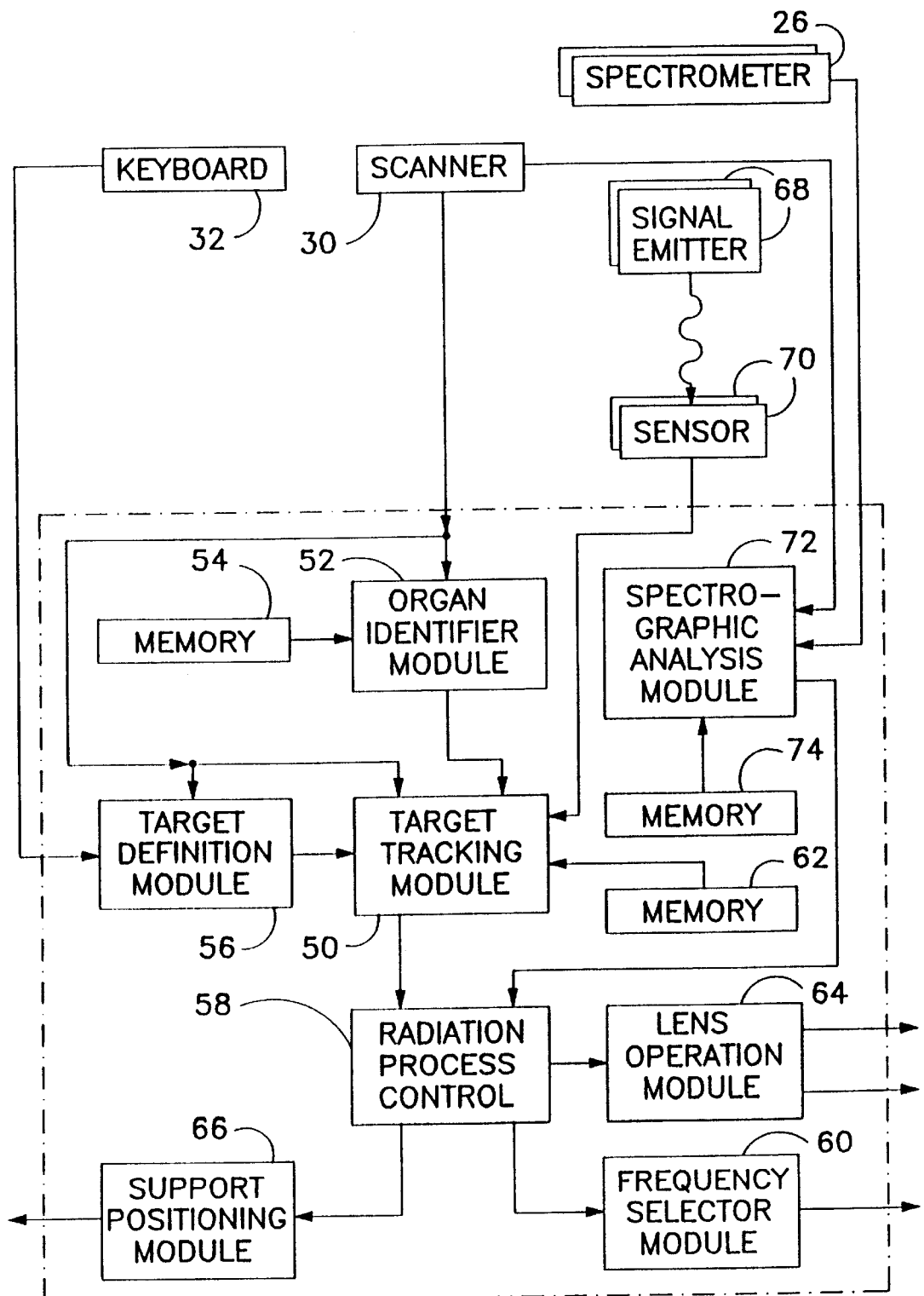
FIG. 2 is a block diagram showing functional components of a computer depicted in FIG. 1.

As illustrated in FIG. 2, computer 28 includes several functional modules which are implemented by generic processor circuits modified by programming to perform specific functions. In particular, computer 28 includes a target tracking module 50 for monitoring and continually updating the location of the predefined target region TR. Target tracking module 50 thus enables the completion of an operation on an internal organ containing the target region TR despite movement or reconfiguration of the organ due to (generally) involuntary muscular contractions of the patient. Target tracking module 50 receives continually updated three-dimensional structural data directly from scanner 30, as well as organ location and shape information from an organ identifier module 52 which is connected at an input to scanner 30. Identifier module 52 accesses a memory 54 for reference data to compare with the real-time three-dimensional data from scanner 30.

Target tracking module 50 is connected at an input to a target definition module 56 which receives instructions from keyboard 32 for defining target region T. Target definition module 56 is also connected to memory 54 and to scanner 30 for enabling a definition of target region TR by computer 28 in accordance with programming for the automatic identification of internal organic structures based on such previously defined parameters as shape, texture, density, and location relative to other organs.

Target tracking module 50 detects when target region TR shifts from an initial location and signals a radiation process control module 58 which then terminates or interrupts the transmission of the selected treatment frequency or frequencies to the patient. To that end, control module 58 is connected to a frequency selector module 60 in turn connected to frequency generators 14 and 16 (FIG. 1) for arresting the emission of the selected treatment frequency or frequencies from frequency generators 14 and 16. Frequency selector module 60 also implements the selection of the different frequencies, for example, one frequency to be produced by generator 14 and another frequency to be produced by generator 16. Frequency selector module 60 additionally implements the setting of treatment parameters including rate of pulsing of the selected treatment frequency or frequencies, the interpulse interval, the pulse duration and the intensity of the radiation. If computer 28 automatically selects the values of radiation parameters radiation process control module 58 sets the parameter values in accordance with instructions communicated via keyboard 32 and treatment tables contained in a memory 62.

Target tracking module 50 can automatically determine new positional coordinates of target region TR after a change in location thereof. This function is particularly useful where internal muscle contractions and other organ movements cause an effectively permanent shift of the target region from the original location. In this case, in response to signals from target tracking module 50, control module 58 automatically redirects the selected treatment frequency or frequencies to the changed location of target region TR in accordance with the new positional coordinates and concentrates the selected treatment frequency or frequencies on the changed location of the target region. Radiation process control module 58 is operatively connected to a lens operation module 64 which is in turn linked to focal point relocation controls 34 and 36 for modifying the focal points of lenses 22 and 24 in response to signals from module 58. A support positioning module 66 is connected to process control module 58 and shifting mechanism 38 for inducing the repositioning of support 12 in accordance with signals from module 58.

A plurality of wireless signal emitters 68 are optionally attached to support 12 for providing computer 28 with reference points for use by target tracking module 50 and organ identifier module 53 to triangulate position coordinates of target region TR and the associated organ. Detectors 70 sense the signals produced by emitters 68 and communicate spatial locations to target tracking module 50 and organ identifier module 52.

As described in U.S. Pat. No. 5,429,144, the disclosure of which is hereby incorporated by reference, the myocardium can be effectively revascularized by inserting stents directly into the myocardium from the left ventricle. The stents define passages or channels which extend from the left ventricle and terminate in the heart wall, thereby enabling the delivery of oxygenated blood from the left ventricle directly to the myocardium, bypassing a blocked coronary artery. In accordance with the disclosure of U.S. Pat. No. 5,429,144, the recesses or channels are formed in the myocardium through the use of intravascular catheters. Those recesses or channels for revascularizing the myocardium may be formed noninvasively with the apparatus of FIG. 1. In such a procedure, target tracking module 50 alerts process control module 58 when the target region, a predefined part of the myocardium, returns to initial position coordinates. Module 58 then automatically redirects the selected treatment frequency or frequencies to the target region. Generally, a target region in the myocardium is irradiated during diastole, i.e., when the heart is relaxed between successive contractions. The myocardium-revascularizing channels or recesses formed in this procedure are capable of remaining open without the use of stents. It may be necessary to perform the radiation-mediated noninvasive operation several times on successive occasions to ensure that the channels remain open. The locations of the channels formed in a patient's heart wall will be stored by computer 28 for possible use by target definition module 56 in subsequent operations.

The radiological treatment apparatus of FIG. 1 optionally includes a photodetector assembly or spectrometer assembly 26 comprising a plurality of individual photodetectors or scanning spectrometers 26a, 26b, 26c, 26d disposed proximately to patient support 12 for detecting electromagnetic radiation ER from the patient P. Radiation ER is emitted from organic cellular material at focal point FP in response to excitation of the cellular material by the treatment frequency or frequencies, e.g., microwaves ME1 and ME2. Generally, some of the target molecules in target region TR which absorb the incoming microwaves ME1 and ME2 are excited to photoluminesce and emit radiation ER. A part of radiation ER escapes through overlying organic tissues of the patient P and is detectable by photodetector assembly or spectrometer assembly 26.

As discussed above, the cells containing the excited molecules are generally destroyed upon excitation by the treatment frequency or frequencies, such as microwaves EM1 and EM2. However, the focus is controlled by lenses 22 and 24 to limit the area which is affected in any one excitation step. The size of focal point FP is also limited in part by pulsing the electromagnetic treatment energy.

Computer 28 includes a spectrographic analysis module 72 which is operatively connected to photodetector assembly 26 for analyzing the signals from the photodetector assembly to ascertain a spectral output of the organic cellular material which lumninesced at focal point FP. Inasmuch as the spectral content of the escaping radiation ER is differentially modified by the tissues through which the radiation passes, computer 28 is programmed to approximate the original spectral content of the radiation emitted by the excited molecular or cellular material at focal point FP. To that end, computer 28 is previously programmed to store, in a memory 74, known absorption spectra for different kinds of tissue. In addition, spectrographic analysis module 72 is provided with three-dimensional structural data from scanner 30 and organ shape and location information from organ identifier module 52 as to the organs of patient P surrounding target region TR. From the kinds and thicknesses of the tissues between focal point FP and a respective unit 26a, 26b, 26c, or 26d of photodetector assembly 26, computer 28 is able to reconstruct the original spectral content of the radiation ER emitted in a photoluminescence process by the excited organic material at focal point FP. Photodetector assembly 26 may include an array of individual photodetectors (not shown), as described in U.S. Pat. No. 5,305,748, the disclosure of which is hereby incorporated by reference.

Spectrographic analysis module 72 determines when a change in spectral output of target region TR has occurred during irradiation thereof with one or more selected treatment frequencies. The change indicates that the molecules available for absorbing the selected treatment frequency or frequencies have been depleted. Radiation process control module 58 is operatively connected to spectrographic analysis module 72 for receiving a signal therefrom indicating a change in spectral output of the target tissues in response to the selected treatment frequency or frequencies. Upon receiving such a signal, module 58 interrupts the generation and directing of each selected treatment frequency to the target tissues.

Figure 3:
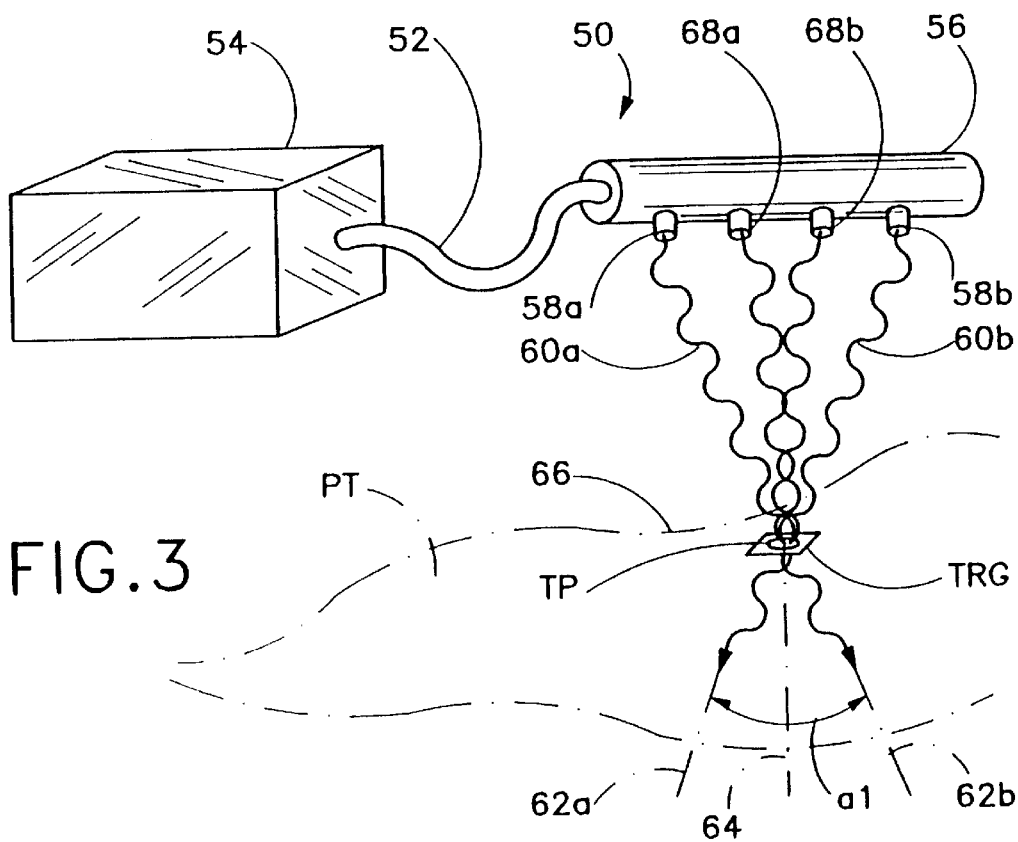
FIG. 3 is a schematic perspective view of another medical treatment type medical system in accordance with the present invention.

As illustrated in FIG. 3, a medical tissue investigation and treatment system comprises a hand held unit or portable transceiver device 150 connected via a waveguide cable 152 to a main housing unit 154. Hand held unit 150 includes a casing 156 provided with a plurality of spaced output ports 158a and 158b for the transmission of collimated electromagnetic radiation 160a and 160b along respective lines 162a and 162b extending through a patient PT. Lines 162a and 162b are coplanar and intersect one another at a predeterminable target point TP inside a target region TRG. Lines 162a and 162b extend at variable angle a1 with respect to one another, as described below. Angle a1 may change so that test point TP moves along a line 164. Line 164 will coincide with line 162a or 162b in the event that the direction of transmission of radiation 160a or 160b remains constant while the direction of transmission of radiation 160b or 160a varies to change angle a1. Generally, line 164 extends perpendicularly to an external surface of patient PT at a point 166 indicated by a patient as being the location of pain.

Casing 156 is optionally provided with a plurality of input ports 168a and 168b containing respective photodetectors 170*a* and 170*b* (FIG. 4) or optical elements (not shown) for transmitting incoming radiation to the photodetectors.

Figure 4:
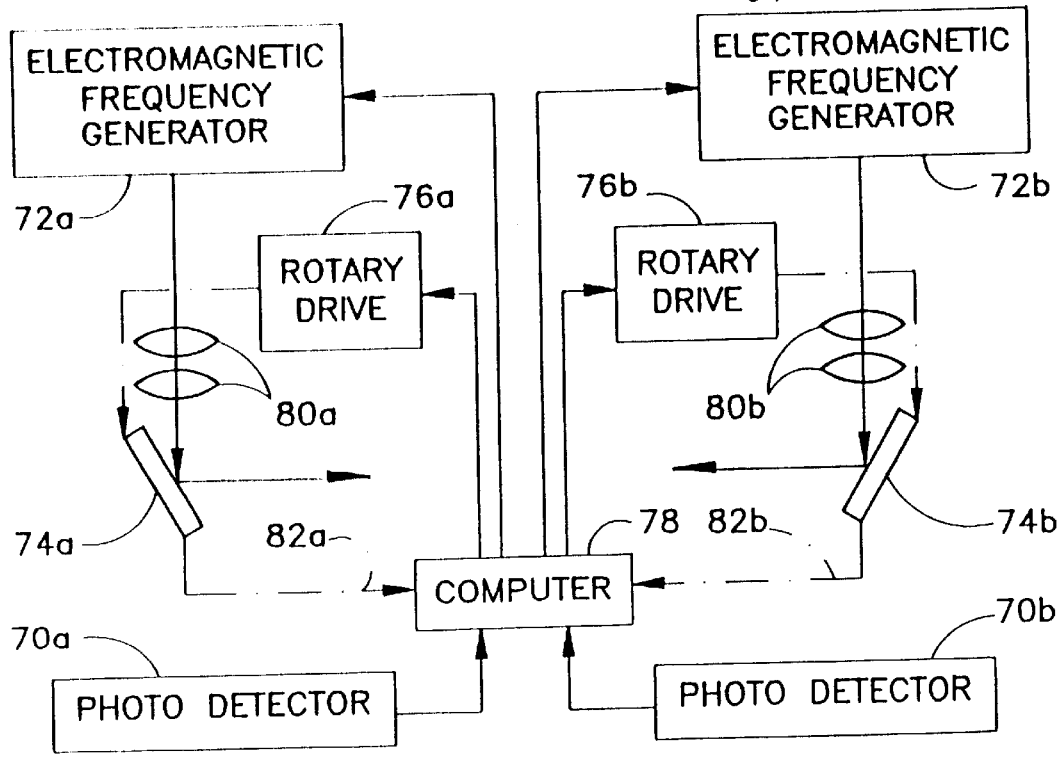
FIG. 4 is a block diagram of functional components of FIG. 3.

As illustrated in FIG. 4, the medical tissue investigation system of FIG. 3 further comprises a first generator 172*a* for generating generally monochromatic electromagnetic energy or radiation 160*a* having a predetermined first treatment frequency in the microwave, near millimeter, infrared, optical, ultraviolet regions of the electromagnetic spectrum. Generator 172*a* is disposed in housing unit 154 and is connected to a first directional transmitter 174*a* disposed, for example, at output port 158*a* for transmitting the first frequency along line 162*a*. A second generator 172*b*, also disposed in housing unit 154, generates electromagnetic energy or radiation 160*b* having a predetermined second frequency different from the frequency of energy or radiation 160*a*. A second directional transmitter 174*b* is disposed at output port 158*b* in casing 156 for transmitting the second frequency 160*b* along line 162*b*.

As illustrated schematically in FIG. 4, directional transmitters 174*a* and 174*b* may take the form of reflectors which are provided with respective rotary drives 176*a* and 176*b* for turning the reflectors to vary the directions of propagation of frequencies or radiation 160*a* and 160*b* (FIG. 3), i.e., for varying the orientations of lines 162*a* and 162*b* relative to casing 156 and relative to the patient PT.

Where photoelectric detector or photodetectors 170*a* and 170*b* are included, they are arranged in an array, e.g., on casing 156, for automatically detecting electromagnetic radiation emitted from organic cellular material in region TRG in response to excitation of the cellular material by the first frequency or radiation 160*a* and the second frequency or radiation 160*b* upon simultaneous irradiation of the tissues at point TP by frequencies 160*a* and 160*b*.

As illustrated in FIG. 4, a computer 178 is operatively connected to photodetectors 170*a* and 170*b* for automatically determining a spectral output or a change in spectral output of the organic cellular material in region TRG from electromagnetic radiation received from the predetermined point TP through the patient PT.

Computer 178 is operatively connected to frequency generators 172*a* and 172*b* for selecting the output frequencies thereof so that the frequencies are absorbable by cellular material contained in target region TRG. Thus, the system of FIGS. 3 and 4 is able to subject any test or target point TP to a multitude of different frequencies. Computer 178 is also connected to rotary drives 176*a* and 176*b* for controlling the operation thereof. Accordingly, computer 178 determines the locations of successive target points, as well as the treatment frequencies to which the cellular material at the target points TP is subjected.

Electromagnetic frequency generators 172*a* and 172*b* may be laser sources producing output radiation transmitted along optical fibers of cable 152 (FIG. 3) to collimating lenses 180*a* and 180*b*, e.g., in casing 154, upstream of directional reflectors 174*a* and 174*b*. At any one time, generators 172*a* and 172*b* may produce the same frequency. In that case, radiation 160*a* and 160*b* combine at the target point TP to provide a sufficient intensity for not only for stimulating or exciting organic molecules within test region TRG but for degrading and destroying those molecules. The location of target region TRG or target point TP is determinable by a scanner such as scanner 30 in FIG. 1. Alternatively, an optical scanner with pattern recognition (see FIG. 5) may function in combination with an ultrasonic or infrared distance scanner (FIG. 5) to automatically determine the location of target region TRG or target point TP.

The scanned is operatively connected to computer 178 for providing the computer with three-dimensional structural data pertaining to the patient's internal organs. As discussed above with reference to FIGS. 1 and 2, computer 178 includes modules for tracking target point TP and automatically halting the transmission of treatment frequencies in the event of a shift in location or shape of an internal organ containing target point TP. Additionally, the target point tracking module of computer 178 enables the computer to continually or periodically transmit a treatment frequency or frequencies to target point TP despite a movement of the target point and output ports 158*a* and 158*b* relative to one another.

In an alternate mode of operation of the medical treatment system of FIGS. 3 and 4, computer 178 controls generators 172*a* and 172*b* to produce radiation 160*a* and 160*b* of different frequencies or wavelengths. The absorbance spectra of organic tissues in region TRG excited by such multiple frequencies or wavelengths will differ from the spectra of tissues subjected to either frequency by itself. Thus, the use multiple frequencies increase the specificity of treatment possible with a noninvasive radiation treatment device as described herein.

Figure 5:
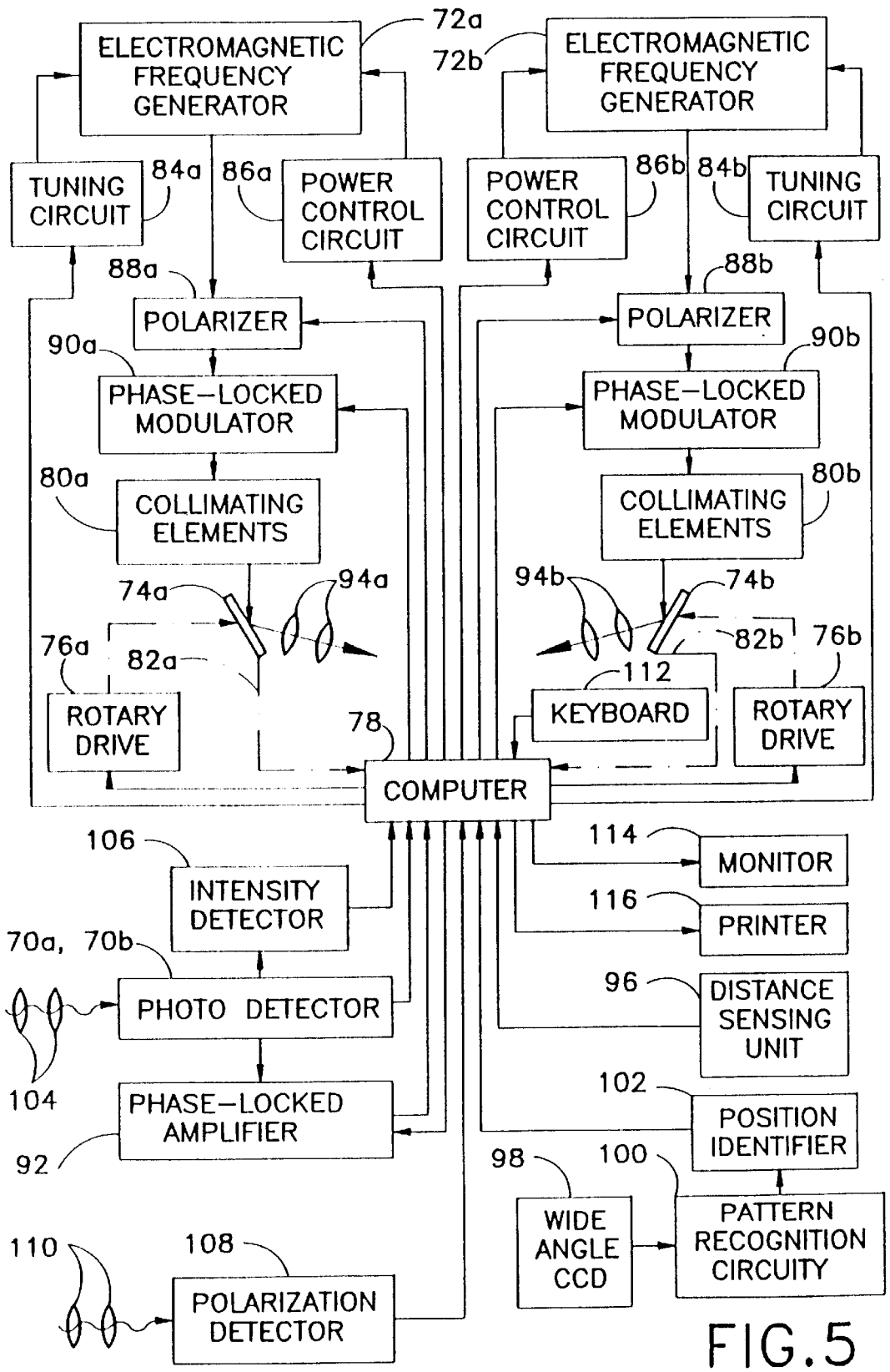
FIG. 5 is a block diagram showing a modified embodiment of the medical treatment system of FIGS. 3 and 4.

The transmission of multiple treatment frequencies, which impinge upon the same organic tissues only at the target point TP, can provide information to computer 178 as to the location of the organic tissues, as described in greater detail hereinafter with reference to FIG. 5. Computer 178 is provided with feedback 182*a* and 182*b* as to the angles of directional transmission reflectors 176*a* and 176*b*, thereby enabling computation of the location of test region TRG. Components in FIG. 5 which are the same as components in FIG. 4 bear the same reference designations. FIG. 5 shows additional componentry for enhancing the operation of the medical investigative and diagnostic system of FIGS. 3 and 4.

As illustrated in FIG. 5, computer 178 is connected at outputs to tuning circuits 184*a* and 184*b* which are in turn connected to respective generators 172*a* and 172*b* for varying, in response to control signals from computer 178, the frequencies of the radiation 160*a* and 160*b* (FIG. 3) produced by generators 172*a* and 172*b*. In addition, computer 178 is linked at outputs to power control circuits 186*a* and 186*b* which in turn are coupled to generators 172*a* and 172*b* for varying the intensity or amplitude of radiation 160*a* and 160*b* produced by generators 172*a* and 172*b* pursuant to signals from computer 178.

Polarizers 188*a* and 188*b* are disposed at the outputs of generators 172*a* and 172*b* for varying the polarization of the radiation produced by the generators. Polarizers 188*a* and 188*b* are adjustable in response to signals from computer 178. Polarizers 188*a* and 188*b* may incorporate componentry for controlling the phase of the generated test frequencies in response to signals from computer 178.

As further illustrated in FIG. 5, phase locked modulators 190*a* and 190*b* are provided at the outputs of generators 172*a* and 172*b* for modulating the output frequencies or radiation thereof in response to signals from computer 178. Modulators 190*a* and 190*b* may operate electrically via modulation of an optical crystal, mechanically via a gating device or chopper, or electronically in the case of microwave emissions. Modulators 190*a* and 190*b* cofunction with a demodulating phase-locked amplifier 192 to filter out extraneous background noise in incoming electromagnetic radiation generated by organic matter in response to the output frequencies or wavelengths of generators 172*a* and 172*b*.

Computer 178 is operatively linked to modulators 190a and 190b and to amplifier 192 for possibly modifying the modulating signal.

Modulated frequencies or waveforms from modulators 190a and 190b are collimated by elements 180a and 180b and directed by reflectors 174a and 174b to a selected target region TRG (FIG. 3). Supplementary focusing elements 194a and 194b may be provided at output ports 158a and 158b (FIG. 3) for focusing the modulated frequencies 160a and 160b at target point TP. Focusing elements 194a and 194b may be controlled by computer 178 to adjust the target point TP.

It is to be noted that the frequencies produced by generators 172a and 172b for exciting target organic tissues span from the ultraviolet through the visible and infrared to microwave frequencies at approximately 30 GHz. It is to be noted further that more than two output ports 158a and 158b may be provided on casing 156. Multiple output ports may be connected to the same frequency generator 172a or 172b. Moreover, the componentry of FIG. 5 may be provided in a stationary installation where hand held casing 156 (FIG. 3) is omitted.

As indicated schematically by dot-dash lines at 182a and 182b, signal generators may be operatively connected to directional reflectors or transmitters 174a and 174b for producing electrical signals encoding a first angle identifying line 162a (FIG. 3) and a second angle identifying line 162b. Computer 178 is operatively connected to the signal generators for computing a location of test or target point TP relative to patient PT in response to the electrical signals.

To further facilitate this locating process, a distance sensing unit or scanner 196 is disposed in hand held unit 150 and is connected to computer 178. Distance sensing unit or scanner 196 incorporates ultrasonic or infrared distance sensors (not separately illustrated) to automatically determine the distance of the patient PT from casing 156. Concomitantly, computer 178 is able to determine the location of test region TRG or test point TP within the patient from the information regarding the location of the patient relative to hand held unit 150 and the location of the test region TRG relative to the hand held unit.

Further locating componentry in the form of a wide angle camera (e.g., a charge coupled device or CCD) 198 may be provided on hand held unit 50. Camera 198 is connected to a pattern recognition circuit 200 and a position identification component 202 which cofunction to determine over what part of the patient PT point TP is located. Pattern recognition circuit 200 and position identification component 202 are incorporated into or connected to computer 178 for facilitating the locating function thereof.

In the system of FIG. 5, computer 178 controls generator 172a and/or generator 172b via tuning circuit 184a or 184b, via power control circuit 186a or 186b for generating electromagnetic energy characterized by a preselected wavelength and a preselected amplitude. In addition, computer 78 can control the polarization of the electromagnetic radiation via polarizer 188a or 188b. Any one or all of these radiation parameters can be varied for optimizing treatment of organic tissues in test or target region TRG (FIG. 3). In addition, by controlling the orientation of directional reflectors or transmitters 174a and 174b (and optionally, the orientations of focusing elements 194a and 194b), computer 178 can test organic spectral responses at different test points TP.

As further illustrated in FIG. 5, radiation collecting elements 204 are disposed upstream of photodetectors 170a, 170b for enhancing the sensitivity thereof. On a downstream or output side, photodetectors 170a, 170b are connected to an intensity detector 206 which measures the intensity of different wavelengths detectable by photodetectors 170a, 170b. Intensity detector 206 is connected to computer 178 for informing that unit of intensity or amplitude measurement results and, particularly, of a change in intensity or measurement results which indicates a depletion of target molecules in target region TRG.

It is to be noted that photodetectors 170a, 170b may be individually tuned to respective frequencies. Photodetectors 170a, 170b, together with intensity detector 206 and computer 178, thus cofunction as a spectrometer for determining the spectral output or a respective tissue sample in a patient PT.

Computer 178 may select intensity or amplitude measurement results which conform to a modulation signal, as sensed by amplifier 192. In additional, a polarization detector or analyzer 208 with concentrating input elements 210 is connected to an input of computer 178 for providing the computer with data pertaining to the polarization characteristics of incoming radiation arriving from irradiated regions of the patient.

The transmission of multiple treatment frequencies, which impinge upon the same organic tissues only at the target point PT, can provide information to computer 178 as to the location of the organic tissues, as described in greater detail hereinafter. Computer 178 is provided with feedback 182a and 182b as to the angles of directional transmission reflectors 176a and 176b, thereby enabling computation of the location of test region TRG.

As discussed hereinabove with reference to FIGS. 3 and 4, the investigative system may transmit two different frequencies through a patient to a target point TP or test region TRG. Each frequency or radiation beam 160a and 160b is transmitted along its respective line or path 162a and 162b. Lines 162a and 162b extend through the patient at angle a1 relative to one another. The angle a1 is determinable by computer 178 by input 182a and 182b regarding the orientations of directional reflectors or transmitters 174a and 174b. Frequencies or radiation beams 160a and 160b are transmitted simultaneously.

The determination of which treatment frequencies are to be used for performing a particular operation on selected target tissues is made in accordance with information as to tissue spectral responses. These spectral responses are collected as described in U.S. Pat. No. 5,482,041, the disclosure of which is hereby incorporated by reference.

The principle underlying this methodology is that the spectral absorbance spectrum of a particular organic molecule, and or atoms included in that molecule, will change depending on the multiple excitation frequencies used. Thus, molecules or a certain kind located at points irradiated by only one of the two frequencies will have a different absorbance spectrum than those molecules of the same kind located at the commonly irradiated (predetermined) target point. This difference enables a fine tuning of noninvasive treatment.

The medical treatment system of FIG. 5 may be used in conjunction with a wireless imaging device such as scanner 30 (FIG. 1) connected to computer 178 as discussed above. That wireless imaging device is used in part to ascertain the location of test point TP relative to the subject's internal anatomy.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A noninvasive medical treatment system comprising:

a support for supporting a patient in a predetermined position;

a frequency generator for generating essentially monochromatic electromagnetic energy of a frequency absorbable by a kind of organic molecule found in predetermined target tissues internal to the patient;

selection means operatively connected to said frequency generator for selecting said frequency from among a plurality of different treatment frequencies produceable by said frequency generator and predetermined to be absorbable by organic molecules of respective types specific to a plurality of different kinds of human tissue;

concentrating means disposed between said frequency generator and said support for directing said energy from said frequency generator to said predetermined target tissues internal to the patient supported on said support and for concentrating said energy on said target tissues;

a scanner disposed proximate to said support for obtaining three-dimensional data as to an organic structure internal to the patient, said organic structure including said target tissues, said scanner including means for continually updating said three-dimensional data during a medical treatment procedure; and a computer operatively connected to said scanner for continually monitoring location and shape of said organic structure during said medical treatment procedure, said computer being operatively connected to at least one element taken from a group consisting essentially of said frequency generator, said concentrating means and said support for controlling said one element in response to said three-dimensional data from said scanner during said medical treatment procedure so that said energy impinges on said target tissues for sufficient time to effectively eradicate said target tissues, whereby said medical treatment procedure is performed despite movement of said organic structure during said medical treatment procedure.

2. The system defined in claim 1 wherein said computer includes means for identifying a location and a shape of said organic structure after a shift of said organic structure, based upon said three-dimensional data from said scanner, said computer further including means for determining a change in positional coordinates of said target tissues due to said shift of said organic structure and for determining an operational modification of said one element for delivering said energy to said target tissues after said shift of said organic structure.

3. The system defined in claim I wherein said concentrating means includes a focusing element.

4. The system defined in claim 3 wherein said one element is said concentrating means, further comprising means operatively connected to said computer and said focusing element for refocusing said element in response to a signal from said computer after a shift of said organic structure.

5. The system defined in claim 1 wherein said concentrating means includes means for directing the selected frequency from different directions to said target tissues.

6. The system defined in claim 1 wherein said one element is said frequency generator, further comprising means operatively connected to said computer and said frequency generator for interrupting transmission of the selected frequency from said frequency generator in response to a signal from said computer after a shift of said organic structure.

7. The system defined in claim 1 wherein said one element is said support, further comprising means operatively connected to said computer and to said support for moving said support in response to a signal from said computer after a shift of said organic structure.

8. The system defined in claim 1 wherein said concentrating means includes means for enabling a change in the location of said predetermined point, said one element being said concentrating means.

9. The system defined in claim I wherein said energy is microwave energy.

10. The system defined in claim 9 wherein said frequency generator includes a plurality of microwave generators, said concentrating means including a plurality of microwave lenses associated with respective ones of said generators.

11. The system defined in claim 9 wherein said frequency generator includes means for emitting said microwave energy in pulses.

12. The system defined in claim 1, further comprising a photodetector disposed proximately to said support for sensing electromagnetic radiation emitted from said target tissues in response to excitation of said target tissues by said selected treatment frequency upon concentrating thereof on said target tissues.

13. The system defined in claim 12 wherein said computer is operatively connected to said photodetector for detecting a change in spectral output of said target tissues in response to said selected treatment frequency and for interrupting the directing of said selected treatment frequency to said target tissues upon detecting said change.

14. The system defined in claim 1 wherein said frequency generator is capable of generating essentially monochromatic electromagnetic energy of two frequencies simultaneously, said selection means being operatively connected to said frequency generator for selecting said two frequencies from among a plurality of different treatment frequencies produceable by said frequency generator and predetermined to be absorbable by organic molecules of respective types specific to a plurality of different kinds of human tissue, said concentrating means being disposed between said frequency generator and said support for directing said two frequencies from said frequency generator to said predetermined target tissues internal to the patient supported on said support and for concentrating said energy on said target tissues.

* * * * *